(12) United States Patent
Tachizaki et al.

(10) Patent No.: US 9,063,168 B2
(45) Date of Patent: Jun. 23, 2015

(54) SCANNING PROBE MICROSCOPE AND MEASUREMENT METHOD USING SAME

(75) Inventors: Takehiro Tachizaki, Tokyo (JP);
Toshihiko Nakata, Tokyo (JP);
Masahiro Watanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/009,729

(22) PCT Filed: Apr. 4, 2012

(86) PCT No.: PCT/JP2012/002336
§ 371 (c)(1),
(2), (4) Date: Dec. 6, 2013

(87) PCT Pub. No.: WO2012/137491
PCT Pub. Date: Oct. 11, 2012

(65) Prior Publication Data
US 2014/0165237 A1  Jun. 12, 2014

(30) Foreign Application Priority Data

Apr. 4, 2011  (JP) ................................ 2011-082396

(51) Int. Cl.
| | |
|---|---|
| *G01Q 60/06* | (2010.01) |
| *G01Q 60/18* | (2010.01) |
| *B82Y 20/00* | (2011.01) |
| *B82Y 35/00* | (2011.01) |
| *G01N 21/552* | (2014.01) |
| *B82Y 15/00* | (2011.01) |
| *G01Q 60/22* | (2010.01) |
| *G01Q 70/12* | (2010.01) |

(52) U.S. Cl.
CPC ............... *G01Q 60/18* (2013.01); *B82Y 20/00* (2013.01); *B82Y 35/00* (2013.01); *G01N 21/554* (2013.01); *B82Y 15/00* (2013.01); *G01Q 60/22* (2013.01); *G01Q 70/12* (2013.01)

(58) Field of Classification Search
USPC ....................................................... 850/24, 30
See application file for complete search history.

(56) References Cited

U.S. PATENT DOCUMENTS

| 6,545,276 B1 | 4/2003 | Sasaki |
| 6,911,646 B1 * | 6/2005 | Weitekamp .................. 250/234 |

FOREIGN PATENT DOCUMENTS

| JP | 10-170523 A | 6/1998 |
| JP | 11-316240 A | 11/1999 |

(Continued)

OTHER PUBLICATIONS

Binning, G. et al. Atomic Force Microscope, Physical Review Letters, Mar. 3, 1986, pp. 930-933, vol. 56 No. 9.

(Continued)

*Primary Examiner* — Kiet T Nguyen
(74) *Attorney, Agent, or Firm* — Crowell & Moring LLP (57) ABSTRACT

Disclosed is a measurement method of a scanning probe microscope based upon a measurement method of a scanning probe microscope for observing a shape and an optical property of a sample by exciting near-field light, scanning relative positions of the near-field light and the sample and detecting scattered light by the sample of the near-field light and having a characteristic that the near-field light is modulated to periodically vary the relative positions of the near-field light and the sample and that a frequency of modulation applied to the near-field light and an interference signal generated at a frequency for varying the relative positions of the near-field light and the sample are selectively extracted.

15 Claims, 12 Drawing Sheets

(56) References Cited

FOREIGN PATENT DOCUMENTS

| JP | 2000-199736 A | 7/2000 |
|---|---|---|
| JP | 2001-194286 A | 7/2001 |
| JP | 2010-071871 | 4/2010 |

OTHER PUBLICATIONS

Dunn, Robert C., Near-Field Scanning Optical Microscopy, Chemical Reviews, 1999, pp. 2891-2927, vol. 99 No. 10, American Chemical Society.

Inouye, Yasushi et al., Near-field scanning optical microscope with a metallic probe tip, Optics Letters, Feb. 1, 1994, pp. 159-161, vol. 19 No. 3, Optical Society of America.

Nakata, Toshihiko et al., Nanometer-resolution optical probe using a metallic-nanoparticle-intercalated carbon nanotube, Journal of Applied Physics, Jan. 11, 2011, pp. 1-5, vol. 109, American Institute of Physics.

International Search Report (PCT/ISA/210) dated May 29, 2012 (Two (2) pages).

* cited by examiner

LINE PROFILE

SCANNING PROBE MICROSCOPE AND MEASUREMENT METHOD USING SAME

TECHNICAL FIELD

The present invention relates to a scanning probe microscope and a sample measurement method using the same.

BACKGROUND

As measurement technique of a minimal area, a scanning probe microscope (SPM) is known. Out of scanning probe microscopes, an atomic force microscope (AFM) is widely used for technique for scanning a surface of a sample by controlling a probe an end of which is pointed and enabling the measurement of surface profile in atomic size (refer to Physical Review Letters, vol. 56, No. 9, p. 930). However, in the atomic force microscope, an optical property such as the distribution of a refractive index on a surface of a sample cannot be measured.

In the meantime, in a most advanced minimal semiconductor device, the performance is enhanced by controlling physical properties in units of a nanometer and the physical properties except a shape are required so be measured in units of a nanometer. Besides, in a storage device and others, as a minimal foreign matter is fatal for the operation of the device, the detailed physical property of the foreign matter is required.

Optical spectral measurement is suitable for the measurement of a physical property, heretofore, Raman microscope for Raman spectroscopy and others are developed, and they are widely utilized for analysis. However, in conventional type optical microscope technique, spatial resolution is approximately a few hundreds nm and as the resolution is short for observation in units of nanometer, the details of a foreign matter cannot be observed.

To address these problems and to measure physical information and an optical property of a surface of a sample at high spatial resolution, there is provided a scanning near-field optical microscope (NSOM).

The scanning near-field microscope uses near-field light that leaks from a minute aperture in the size of approximately a few tens nm in means called an aperture probe for example as described in Chemical Reviews, 1999, vol. 99, No. 10, pp. 2891-2927. An optical property of a surface of a sample can be measured at spatial resolution of a few tens nm similar to the aperture by holding clearance between the minute aperture and the sample in a range of a few nm to a few tens nm and scanning the aperture.

Besides, in Optics Letters, vol. 19, no. 3, p. 159, a scanning near-field optical microscope that radiates light to a pointed end of a probe and realizes optical observation at spatial resolution of a few tens nm using near-field light generated at the end of the probe depending upon interaction with a sample and scattered light of the near-field light is also disclosed. This technique is known as a scattering probe.

In the scanning near-field optical microscope, light that leaks from the minute aperture is feeble according to the aperture probe for example and as interaction with the sample is weak in the scattering probe, detected light is feeble, high-precision and sensitive measurement is difficult.

Japanese Unexamined Patent Application Publication No. 1999-316240 discloses a means that intermittently excites near-field light excited at an end of a probe in a scattering probe and realizes sensitive measurement. However, in the technique, it is not settled that excited light itself is directly mixed with observed light and sensitive measurement is difficult. Further, as the excitation of the near-field light is intermittent, there is a problem that the absolute luminous energy used for measurement of near-field light is short and sensitive measurement is basically difficult.

As described above, to measure the optical property at the spatial resolution in units of nanometer, it is effective that the scanning near-field optical microscope is used. However, as described above, there is the problem that sensitive and high-precision measurement is very difficult.

To address this problem, a measurement method of plasmon propagation-type optical SPM disclosed in Journal of Applied Physics, vol. 109, no. 1, p. 013110 can be given. In the plasmon propagation-type optical SPM, light is radiated to a cantilever so as to excite plasmon and near-field light is generated at the forefront of a probe. As the near-field light excited at the forefront of the probe is scattered when the near-field light approaches a sample or is touched to the sample, measurement is made by observing scattered light as propagated light in a distant place. In this technique, as light is measured in synchronization with the oscillation of the cantilever, the scattered light is detected at a frequency of the oscillation of the cantilever.

SUMMARY

However, in the above-mentioned plasmon propagation-type optical SPM, not only light to be properly measured that results from near-field light excited at the end of the probe but light for controlling the cantilever, background light and others mix as frequency components included in measured light and synchronized with (having the same frequency as) the oscillation of the cantilever. Therefore, when measurement is made at a frequency for oscillating the cantilever, much noise is superimposed, measurement precision and sensitivity are deteriorated.

Plasmon excitation light can be separated from control light and others using a wavelength filter by making the light a wavelength different from others, the control light and others can be removed, however, it is not always possible. Besides, background light and others can be also removed by using a spatial filter to some extent, however, all cannot be removed. In addition, as a frequency for oscillating the cantilever is approximately a few hundred kHz, it is included in a frequency band in which much electric noise is caused in measurement equipment, many noise sources except light are included, and the enhancement of sensitivity is generally difficult.

A purpose of the present invention is to provide a measurement method of a scanning probe microscope that measures a shape and an optical property of a sample using near-field light without deteriorating signal-to-noise ratio in the plasmon propagation-type optical scanning probe microscope (SPM) in view of the above-mentioned problem.

To address the problem, the present invention provides a measurement method of a scanning probe microscope based upon a measurement method of a scanning probe microscope for observing a shape and an optical property of a sample by exciting near-field light, scanning relative positions of the near-field light and the sample and detecting scattered light by the sample of the near-field light and having a characteristic that the near-field light is modulated, relative distance between the near-field light and the sample is periodically varied and an interference signal generated by a frequency of modulation applied to the near-field light and a frequency for varying the relative distance between the near-field light and the sample is selectively extracted.

Besides, the present invention in another viewpoint provides a scanning probe microscope provided with a near-field light exciting laser that excites near-field light, a cantilever that scans relative positions or the near-field light and a sample, a modulating means that modulates the near-field light a photodetector that has a filter which selectively transmits a predetermined frequency and detects scattered light by the sample of the near-field light and a controller that periodically oscillates the cantilever.

According to the present invention, the measurement method of the scanning probe microscope that measures a shape and an optical property of a sample using near-field light without deteriorating signal-to-noise ratio can be provided in the plasmon propagation-type optical PPM.

DETAILED DESCRIPTION

In conductive material, a free electron exercised or oscillated on a macroscopic scale is called a plasmon and the concentration in the vicinity of a surface of plasmons is called a surface plasmon. The surface plasmon can be excited by the irradiation of light, a coupled wave of a plasmon and light is called plasmon polariton, and the plasmon polariton can involve the energy of light used for excitation. Besides, the plasmon polariton can be converted to light (including an electromagnetic field and near-field light) according to a condition and the light can be led to an area which cannot be directly reached by light using this property.

In the present invention, a method of leading light to nanostructure utilizing the property of the plasmon polariton and optically observing the nanostructure will be described. An embodiment of the present invention will be described referring to the drawings below.

First, measurement operation will be described using a concrete configuration example of a device shown in FIG. 1.

A cantilever 102 having conductive nanostructure 101 at an end is irradiated with laser light 901 for exciting plasmon polariton (near-field light) 900 by a laser 103 as a near-field light exciting laser. Relative positions of near-field light and a sample are scanned using the cantilever 102. The laser light 901 is focused on the vicinity of the nanostructure 101 at the end of the cantilever 102 by a lens 104. The height, the torsion and an oscillated state of the cantilever 102 are monitored by a sensor 105 and a controller 106 controls relative distance between the cantilever 102 and the sample 108 and a condition of a touch by controlling a scanner 107 using a result of monitoring. The sample 108 is mounted on a sample stage 109 and the sample stage three-dimensionally changes the relative positions of the sample and the cantilever 102.

The nanostructure 101 is made of a carbon nanotube (CNT), metal nanowire, a metal nanoparticle or a nanostructure including carbon nanotube for example. The above-mentioned can be selected in consideration of the efficiency of near-field, light excitation by the plasmon polariton 900, the facility of fixture to the cantilever 102, an optical and mechanical property of the nanostructure.

A semiconductor laser, a gas laser or a solid-state laser for example can be used as a source for generating the laser 103 and for the wavelength, ultraviolet rays, visible radiation light or infrared light can be used in consideration of the efficiency of the excitation and the output of near-field light. Depending upon the required intensity of near-field light and the efficiency of the excitation of near-field light, not the laser but a light emitting diode (LED), a lamp which is a source of white light or others can be used. As a band of the emission of the lamp is wide when the lamp is used, the lamp is suitable for spectral analysis.

A capacitive sensor, an optical lever, a tunneling current detector or others can be used for the sensor 105 and can be selected in consideration of required sensitivity and convenience in mounting.

An optical system that observes the end of the cantilever 102 and the position of the sample 108 and observes from the upside of the cantilever 102 to determine a measurement position is provided. The optical system is configured by a light source 110, an image sensor 111, a half mirror 112 and a half mirror 113 and is made coaxial with the laser 103 by the half mirror 113.

The sample 108 is observed using near-field light generated at the end of the cantilever 102 by the plasmon polariton 900 excited by the laser 103. Concretely, as near-field light is scattered to be propagated light, when the end of the cantilever 102 is touched to the sample 108, the scattered light is converged and measurement is made. The scattered light is converged by a detecting lens 114 and is led to a photodetector 116 through an optical element 115. The optical element 115 branches and the transmission of light to a monitor 117 for checking on which area of the sample 108 the detecting lens 114 is focused may be also enabled.

A photomultiplier, a photodiode and a solid-state image sensing device such as CCD for example can be used for the photodetector 116 and can be selected in consideration of a required frequency characteristic and required sensitivity.

The controller 106 is connected to the laser 103, the image sensor 111, the scanner 107, the sample stage 109, the photodetector 116 and the monitor 117, is controlled by PC 118 and controls each equipment, and fulfills a role of transmitting results of measurement and others to the PC 118. The PC 118 is provided with GUI and is provided with a function of transmitting control parameters input by an operator to the controller 106 and a function of displaying results of measurement and others transmitted from each unit of equipment.

Figure 2:
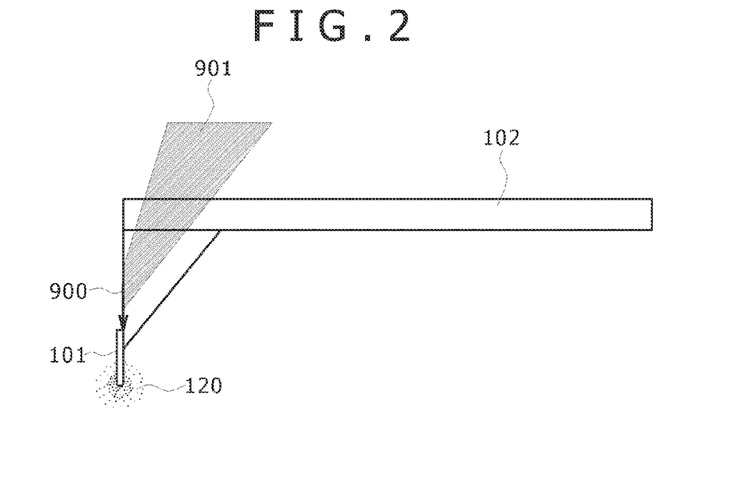
FIG. 2 shows a principle of the generation of near-field light.
Figure 3:
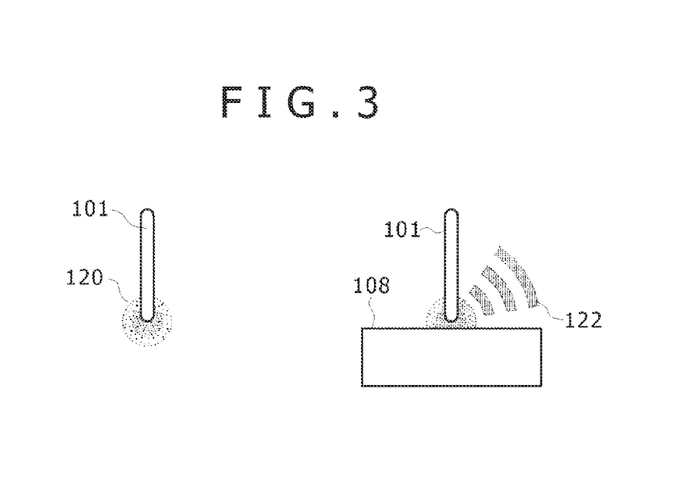
FIG. 3 shows a principle of the measurement of a sample.

Next, a principle of measurement will be described referring to FIGS. 2 and 3. The laser 103 irradiates the cantilever 102 provided with the nanostructure 101 at the end and the plasmon polariton 900 is generated at an edge of the cantilever 102. The plasmon polariton 900 is propagated at the and of the cantilever and is led to the nanostructure 101 provided at the end of the cantilever. When the plasmon polariton 900 propagated in the nanostructure 101 reaches an end of the nanostructure 101, it is converted to light. The light converted at the end of the nanostructure 101 is turned near-field light 120 that locally exists at the end of the nanostructure in a free state in which the end of the nanostructure 101 is touched to nothing (see FIG. 3). In the meantime, when the nanostructure is close to or is touched to any object 121, the near-field light 120 interacts with the object 121 and the near-field light 120 is scattered or the intensity of the near-field light 120 is varied. As the scattered light 122 varies depending upon distance between the nanostructure 101 and the object 121, an optical property and an electric property of the object 121, a shape and materials of the object 121 can be measured by measuring the intensity of the scattered light 122 for example.

Figure 4:
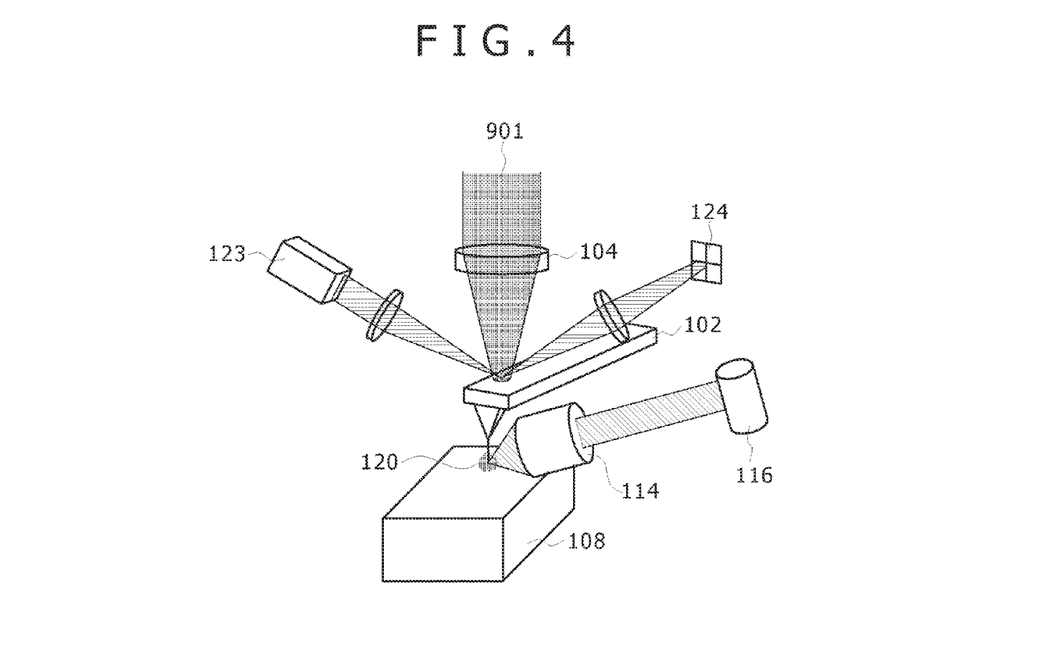
FIG. 4 shows an example of the concrete configuration of a circumference of a cantilever.

FIG. 4 shows an example of the configuration of a periphery of the cantilever 102. The height, the torsion and an oscillated state of the cantilever 102 are observed by the sensor 105 such as the optical lever. The optical lever irradiates the end of the cantilever with radiation focused on the end using a laser and SLD for example for a light source 123 and receives its reflected light by an image sensor 124 such as a partition sensor and PSD. A method of using optical technique such as an optical interferometer and electric technique using a capacitive sensor and tunneling current can be used for the sensor 105 in addition to the optical lever.

Next, a measurement method will be described referring to FIG. 5. The cantilever 102 is oscillated periodically for example by the controller 106 and the closeness or the touch to the sample 108 is repeated at a fixed cycle. However, the cantilever 102 is not necessarily required to be oscillated at a fixed cycle, if the timing of closeness to the sample 108 and the timing of measurement have only to be synchronized, the cantilever is not required to be oscillated at the fixed cycle, and the purpose is achieved. Therefore, it is desirable that a mechanism that enables closeness and recession to/from the sample 108 is provided. Besides, the closeness or the touch to the sample 108 is not required to be made at a fixed cycle or intermittently, and the cantilever and the sample may be also continuously in contact. In this case, measurement has only to be made at arbitrary timing and this case has an advantage that measurement is simple.

Figure 5:
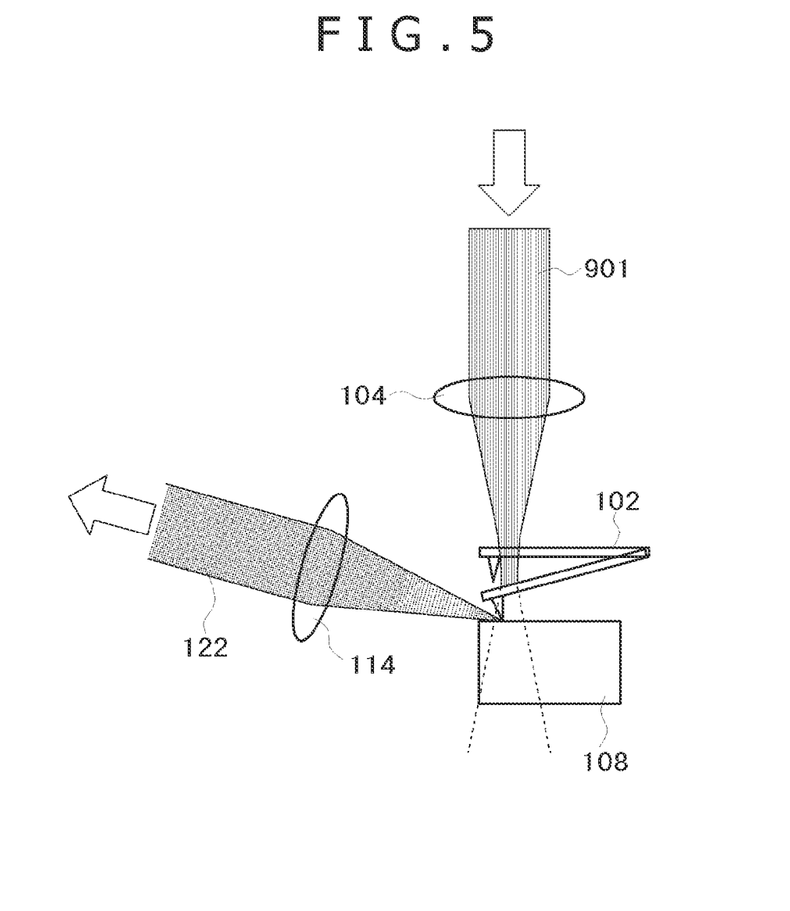
FIG. 5 is a schematic drawing showing the oscillation of the cantilever and the generation of scattered light by the sample.
Figure 6:
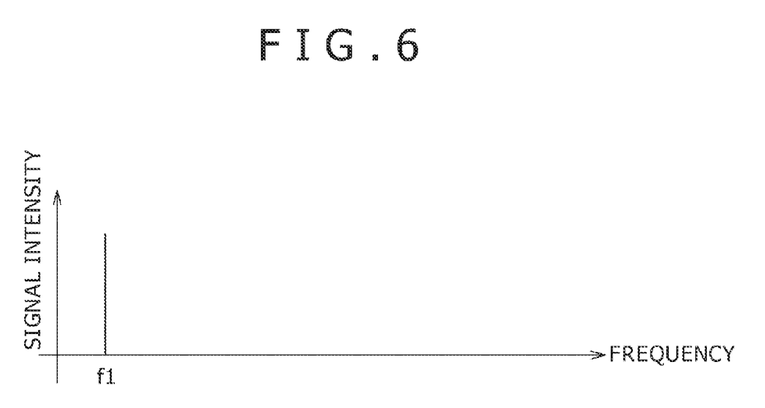
FIG. 6 shows an example of a frequency component of a measured signal acquired when the cantilever is oscillated.

As shown in FIG. 5, when the cantilever 102 is oscillated by the controller 106 to periodically bring the cantilever close to the sample 108 or to periodically touch it to the sample, scattered light 122 measured by the detecting lens 114 is generated at an oscillational cycle of the cantilever 102. Therefore, a measured signal emerges at a cantilever oscillation frequency f1 on a frequency axis as shown in FIG. 6.

A frequency component is separated from a DC component such as background light by generating scattered light 122 at a fixed cycle and selectively acquiring only its frequency component and only a required signal can be acquired. Information related to the oscillation of the cantilever 102 is included in a signal acquired by the method, and the sensitivity and the precision are excellent, compared with a case that the cantilever 102 is continuously brought close to the sample 108 and measurement is made at arbitrary timing.

However, in she meantime, in she measurement according so the above-mentioned method, noise light, caused by the oscillation of the cantilever 102 and electric noise of the same frequency are all detected. In this case, she noise light means scattered light by the cantilever 102 included in light measured by the optical lever when the optical lever is used for the sensor 105 and the variation of background luminous energy by the oscillation of the cantilever 102. The electric noise means an electric signal mixed in a measurement system for driving she oscillation of the cantilever 102 and electric noise intrinsic in a measurement atmosphere. Because of these noises, there occurs a problem that the information of the sample 108 in a measurement result is screened by noise or the separation of signals is difficult because of quantitative measurement.

Then, detection means that applies modulation to the laser 103 or the sample 108 and realizes sensitive and high-precision measurement will be described below.

Figure 1:
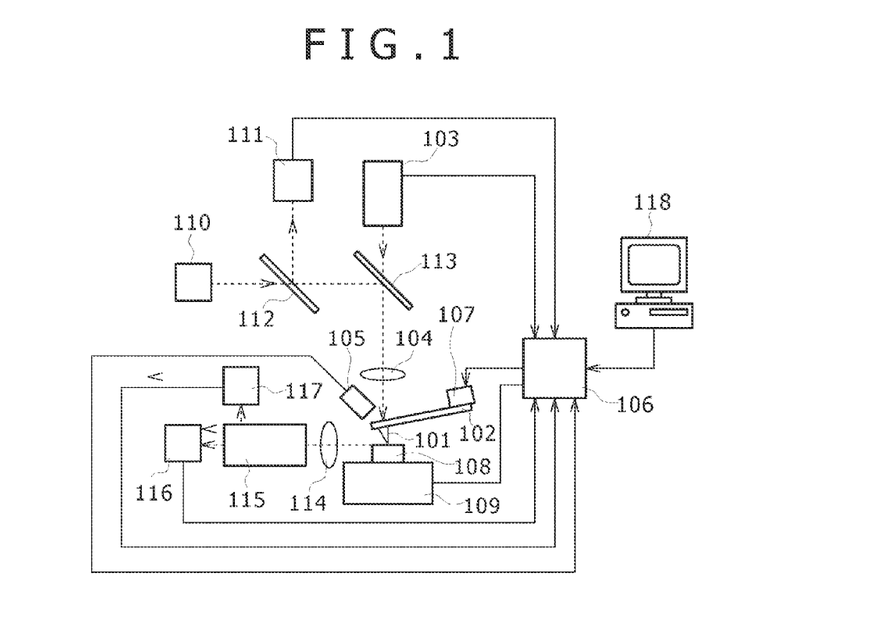
FIG. 1 shows an example of the configuration of a concrete device.
Figure 7:
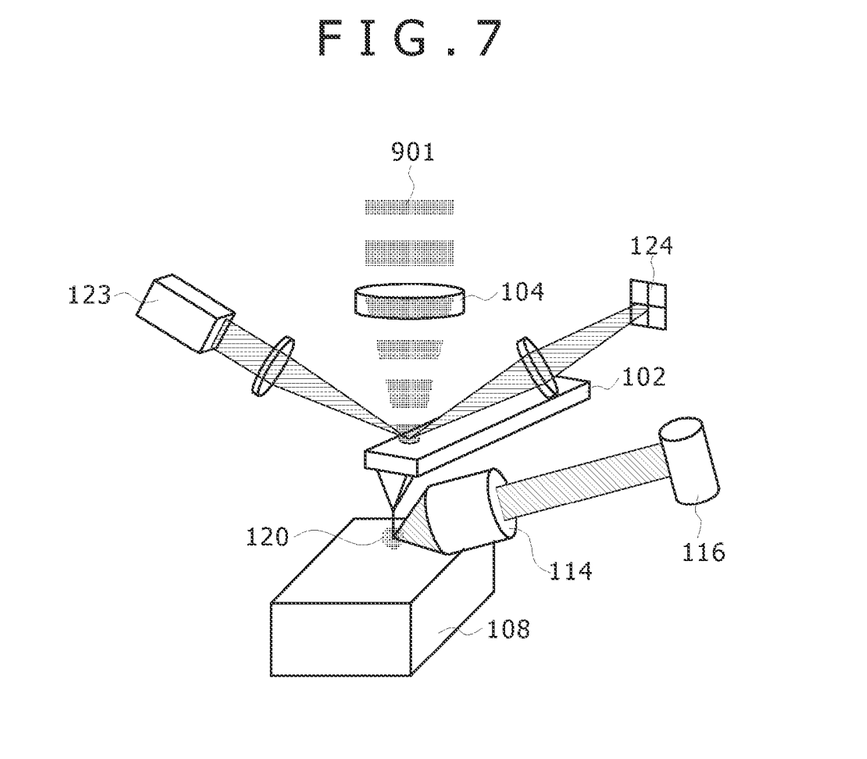
FIG. 7 shows an example of the concrete configuration of the circumference of the cantilever when exciting light is modulated.

An embodiment shown in FIG. 7 schematically shows a case that periodic modulation is applied to the laser 103 based upon the configuration shown in FIG. 1. When amplitude modulation of a frequency f2 for example is applied for modulation applied to the laser 103, near-field light 120 excited at the end of the nanostructure 101 is also intermittently excited at the frequency f2. When such modulation is applied, the oscillation frequency f1 of the cantilever 102 and the modulation frequency f2 of the laser 103 are included in scattered light 122 converged by the detecting lens 114, and when they are detected by the photodetector 116, a signal of frequency components of frequencies 2f1 and 2f2, f1+f2 and |f2−f2| is included (see FIG. 8) because $|\sin(f1t)+\sin(f2t)|^2 = [\sin(2f1t)]/2+[\sin(2f2t)]/2-\cos(f2+f1)t+\cos|f2-f1|t+1 \ldots$ Expression 1.

Figure 8:
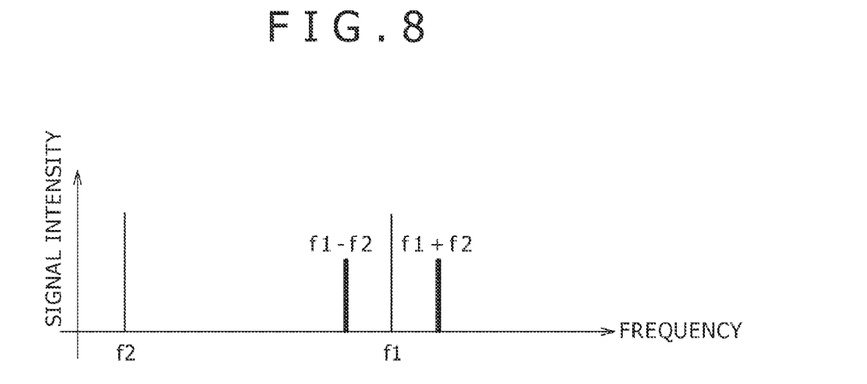
FIG. 8 shows an example of frequency components of a signal acquired when exciting light is modulated.

Only a signal related to both the oscillation of the cantilever 102 and the near-field light 120 can be acquired by selectively extracting only the frequency component of f1+f2 or |f2−f1| out of each frequency component included in the signal. Hereby, the scattered light caused by the oscillation itself of the cantilever included in light measured by the optical lever for example, a cantilever oscillation driving signal and others can be removed.

Besides, as modulation 125 applied to the laser 103 or the sample 108 can be arbitrarily selected in a range of DC to a few tens GHz, there is an advantage that a frequency band substantially without background noise which is suitable for detection is selected and measurement can be made. This is effective in the reduction of electric noise, compared with that the oscillation frequency of the cantilever 102 is a certain fixed frequency. In addition, an oscillation frequency of a general cantilever is approximately 10 to 500 kHz and is relatively a low frequency, while it is also effective in the reduction of electric noise that detection at a high frequency is enabled.

Further, the sample can be measured without a touch, nondestructively and noninvasively by applying modulation to the laser 103 and applying no modulation to the sample 108.

Figure 9:
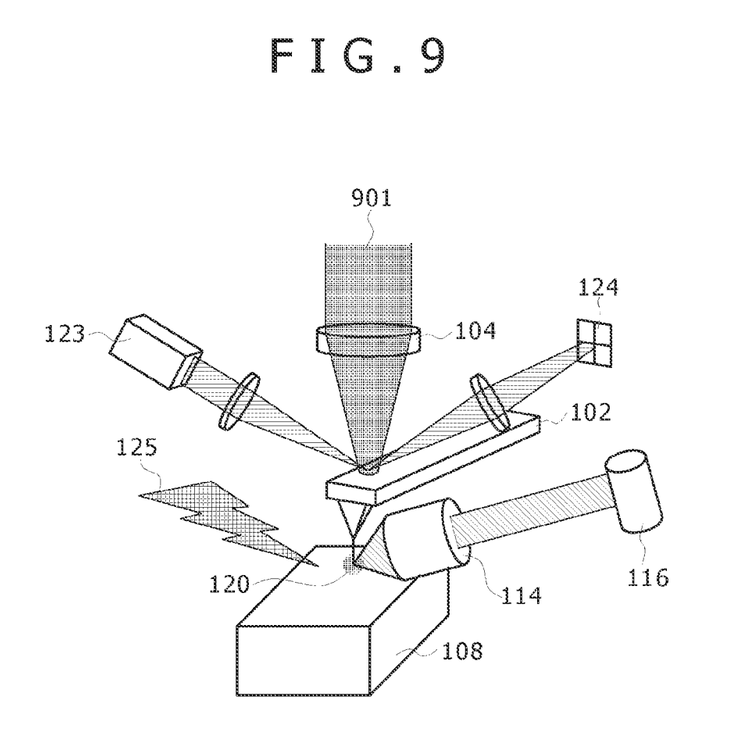
FIG. 9 shows an example of the concrete configuration of a circumference of the cantilever when modulation is applied to the sample.

FIG. 9 shows an example that modulation 125 is applied to the sample 108 by a modulator (not shown) without applying modulation to the laser 103 that excites plasmon polariton 900. For the modulation 125 applied to the sample by the modulator, electric modulation that applies voltage, optical modulation that excites light, dynamic modulation that applies oscillation, thermal modulation that applies heat, chemical modulation that changes a phase and others are conceivable. For an area in which modulation is applied to the sample 108, modulation of required intensity has only to be applied to an area in which the nanostructure 101 and the sample 108 are touched, modulation may be also directly applied to a point at which the nanostructure 101 and the sample 108 are in contact, modulation applied to another location of the sample 108 is propagated, and the propagated modulation may be also indirectly applied to the point of contact of the nanostructure 101 and the sample 108.

A mechanical property of the sample 108 can be measured by applying dynamic modulation to the sample 108 and the thermoelasticity of the sample 108 can be measured by applying thermal modulation to the sample 108. Besides, the electronic and electric property of the sample 108 can be measured by applying electric modulation to the sample 108.

As selection out of more frequency components and measurement are enabled by selecting plural frequencies for the modulation 125 applied to the laser 103 or the sample 108, the frequencies having less background noise can be selected.

Only a signal related to both the oscillation of the cantilever 102 and the near-field light 120 or only a signal related to the oscillation of the cantilever 102 and the sample 108 can be selectively acquired by using the configurations shown in FIGS. 7 and 9. Hereby, optical noise and electric noise respectively caused by the oscillation of the cantilever 102 can be reduced. In the meantime, it is feared that in the configuration shown in FIG. 7, scattered light by the cantilever 102 of the laser light generated by the laser 103 is mixed in the measurement system to be optical noise, and it is feared that in the configuration shown in FIG. 9, when modulation is applied to the sample 108 using light, modulated excitation light is scattered by the sample 108 or the cantilever 102 to be optical noise. When dynamic modulation is applied to the sample 108 in the configuration shown in FIG. 9, it is also feared that the oscillation of the sample 108 has an effect upon the interaction of the cantilever 102 and the sample 108 for example and optical and electric noise is made.

Figure 10:
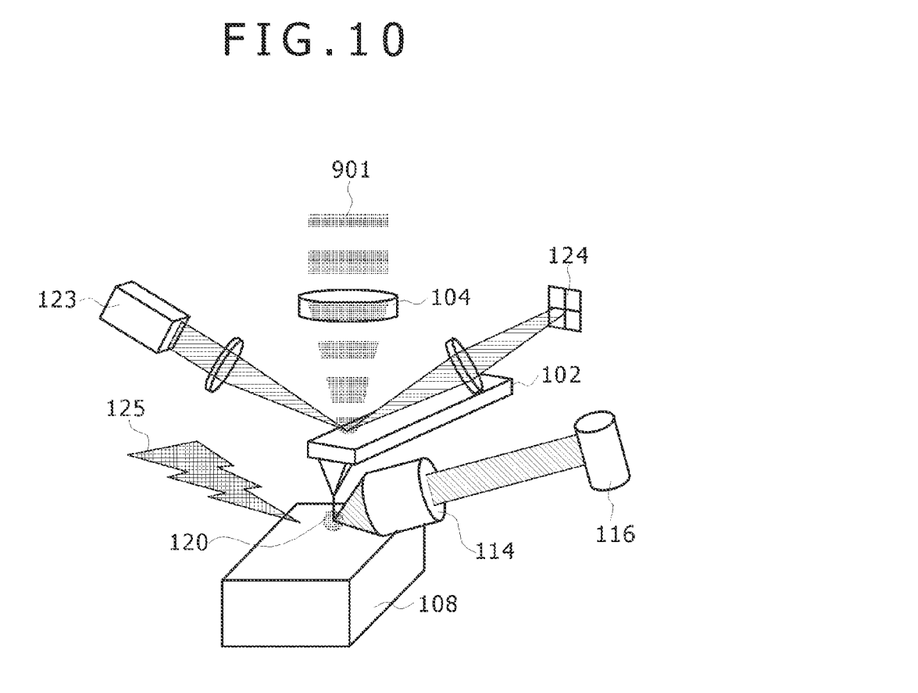
FIG. 10 shows an example of the concrete configuration of a circumference of the cantilever when modulation is applied to exciting light and the sample.

Then, as shown in FIG. 10, detection means that applies modulation to both the laser 103 and the sample 108 and measures only the information of the sample 108 at higher sensitivity and higher precision will, be described below.

FIG. 10 shows an example of configuration when modulation is applied to both the laser 103 and the sample 108.

As selection out of more frequency components and measurement are enabled by selecting plural frequencies in the modulation 125 applied to the laser 103 and the sample 108, the frequencies having less background noise can be selected.

Plural frequencies may be also selected in the modulation 125 applied to the laser 103 and the sample 108, however, a case that the laser 103 that radiates one beam of light for exciting plasmon polariton 900 is modulated at f2 and the sample 108 is modulated at f3 will be described as an example below. The cantilever 102 is oscillated at f1, is touched to the sample 108 in synchronization with an oscillational cycle, and near-field light 120 is scattered at the same time of contact. Then, a signal detected by the photodetector 116 is described as follows.

$$|\sin(f_1 t)+\sin(f_2 t)+\sin(f_3 t)|^2 = 3/2 - \cos(2f_1 t)/2 - \cos(2f_2 t)/2 - \cos(2f_3 t)/2 - \cos(f_1+f_2)t + \cos|f_1-f_2|t - \cos(f_2+f_3)t + \cos|f_2-f_3|t - \cos(f_3+f_1)t + \cos|f_3-f_1|$$ Expression 2

Only a signal related to both the oscillation of the cantilever 102 and the near-field light 120 is included in a frequency component of "f1±f2" out of detected frequency components and hereby, scattered light in light measured by the optical lever and a cantilever oscillation driving signal for example respectively caused by she oscillation itself of the cantilever can be removed.

Figure 11:
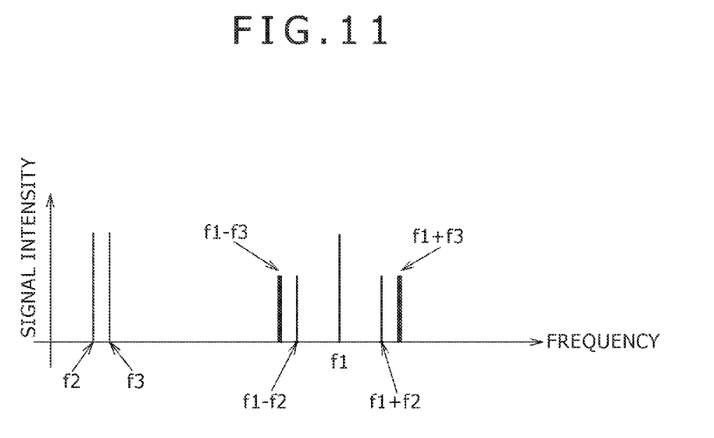
FIG. 11 shows an example of frequency components of measured signal acquired when modulation is applied to the exciting light and the sample.

A frequency component of "f2±f3" includes only information related to the near-field light 120 and the sample 108 and no information related to the cantilever 102 is included (see FIG. 11). Therefore, as optical and electric noise caused by the oscillation of the cantilever can be removed and f2 and f3 can be freely selected, a frequency of "f2+f3" or "|f2−f3|" at which electric noise is minimum can be selected, and the information of the sample 108 can be sensitively acquired. When a frequency component of "f2±f3" is measured, the cantilever 102 is oscillated or moved and is not necessarily required to be intermittently touched to the sample 108, and there is an advantage that only a signal generated by the near-field light 120 and the sample 108 can be selectively acquired even if the cantilever is in contact with the sample 108.

Frequency components of "2f1", "2f2", "2f3", "f1+f2", "f2±f3" and "f3±f1" are included in a signal detected by the photodetector 116 as shown in the expression 2, however, it will be described below that at least two frequency components out of these are extracted by filtering and they are made so interfere by a mixer. For a concrete example, when the frequency components shown in the expression 2, "2f1" and "f2+f3" are extracted by filtering and they are made to interfere by she mixer, frequency components, "2f1+f2+f3", "2f1−f2−f3" and "2f2+2f3" are newly generated because |cos (2f1t)/2−cos(f2+f3)t|^2=cos(2f1)/8+cos (2f2+2f3)/2−cos (2f1+f2+f3)/2−cos(2f1−f2−f3)/2+5/8 . . . Expression 3. As only a signal related to the oscillation of the cantilever 102, the near-field light 120 and the sample 108 is included in the components of "2f1+f2+f3" and "2f1−f2−f3" out of these, sensitive detection in which optical noise and electric noise are sufficiently inhibited is enabled by selectively detecting "2f1+f2+f3" or "2f1−f2−f3" in the signal shown in the expression 3.

Figure 12:
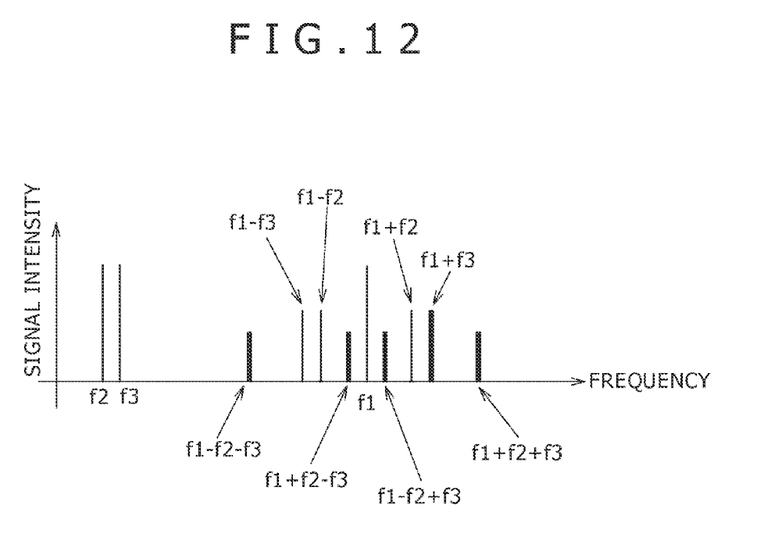
FIG. 12 shows an example of frequency components of a measured signal when modulation is applied to the exciting light and the sample and a high-order interference signal is acquired in the measured signal.

In the meantime, when a photodetector that shows an intense nonlinear response is used for the photodetector 116, scattered light 122 is measured and when it is converted to an electric signal, a high-order beat of input can be generated. When the above-mentioned example is used, a tertiary nonlinear component for example becomes |sin(f1)+sin(f2)+sin (f3)|^3=sin ^3(f1)+sin ^3(f2)+sin ^3 (f3)+3 sin(f1) sin ^2(f2)+3 sin(f1) sin ^2(f3)+3 sin ^2(f1)sin(f2)+3 sin ^2(f1) sin(f3)+3 sin(f2) sin ^2(f3)+3 sin ^2(f2) sin(f3)+6 sin(f1) sin (f2) sin(f3) . . . Expression 4. When a term of sin(f1) sin(f2) sin(f3) in the expression 4 is rewritten, it is turned sin(f1) sin(f2) sin(f3)=[sin(f1+f2+f3)−sin(f1−f2+f3)+sin(f1−f2−f3)−sin(f1+f2−f3)]/4 . . . Expression 5 (see FIG. 12). Hereby, when scattered light 122 is measured by a photodetector having intense nonlinearity, only frequency components caused by the near-field light 120, the oscillation of the cantilever 102 and the sample 108 such as "f1+f2+f3", "f1+f2−f3", "f1−f2+f3" and "f1−f2−f3" can be selectively extracted by extracting a tertiary nonlinear term. Especially, as f2 and f3 can be arbitrarily selected, there is an advantage that a detected frequency can be turned a substantial noiseless band.

The reason why the detection of the high-order beat is enabled in the photodetector having intense nonlinearity is in the method using plasmon polariton that can excite the near-field light 120 at the end of the probe very intensely.

Though the following case is essentially similar to the above-mentioned case, the case that modulation is applied to the excitation of the near-field light 120 at frequencies fa, fb, fc, . . . , modulation is applied to the sample 108 at frequencies f1, f2, f3, . . . and the cantilever 102 is oscillated at fAFM will be considered below. A frequency "f1±f2±f3± . . .

±fAFM±f1±f2±f3± . . . " (Expression 6) is acquired as an electric signal by photodetection having intense nonlinearity. Only information related to the near-field light 120, the cantilever 102 and the sample 108 can be selectively acquired by selectively extracting only the frequency components shown in expression 6, sensitive and high-precision measurement is enabled.

The generation of optical noise by the mixture of scattered light by the cantilever 102 from the laser 103 in the measurement system can be reduced by applying modulation to both the laser 103 and the sample 108. Besides, the generation of optical noise by the scattering on the sample 108 or the cantilever 102 of modulation excitation light can be reduced when modulation is applied to the sample 108 using light. In addition, optical and electric noise caused because the oscillation of the sample 108 for example has an effect on interaction with the cantilever 102 and the sample 108 can be reduced when dynamic modulation is applied to the sample 108.

Figure 13:
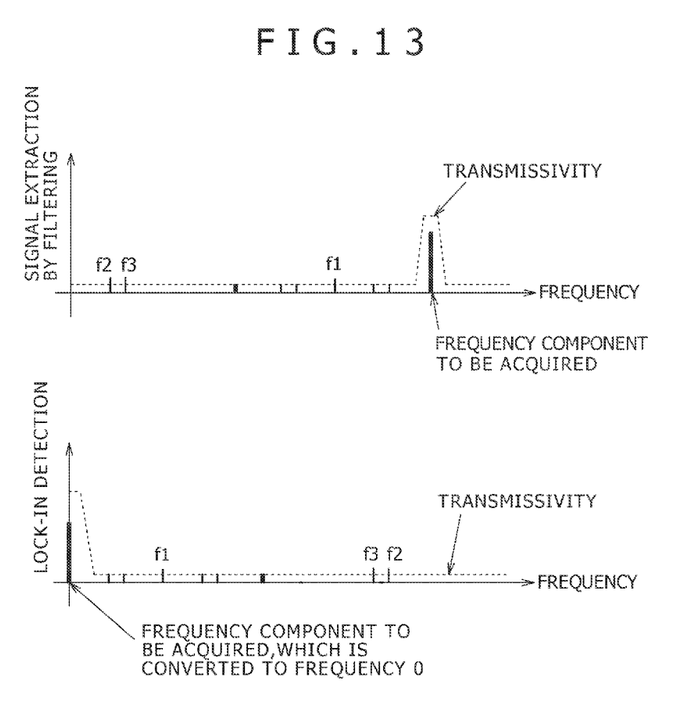
FIG. 13 explains means for acquiring an objective frequency component.

To selectively extract the frequency components described in the expressions 1 to 6, there can be considered a method of using a band-pass filter that selectively transmits only specific frequencies, a method of combining a low-pass filter and a high-pass filter and selecting frequency components and a method by lock-in detection respectively in the photodetector 116 as shown in FIG. 13.

Figure 14:
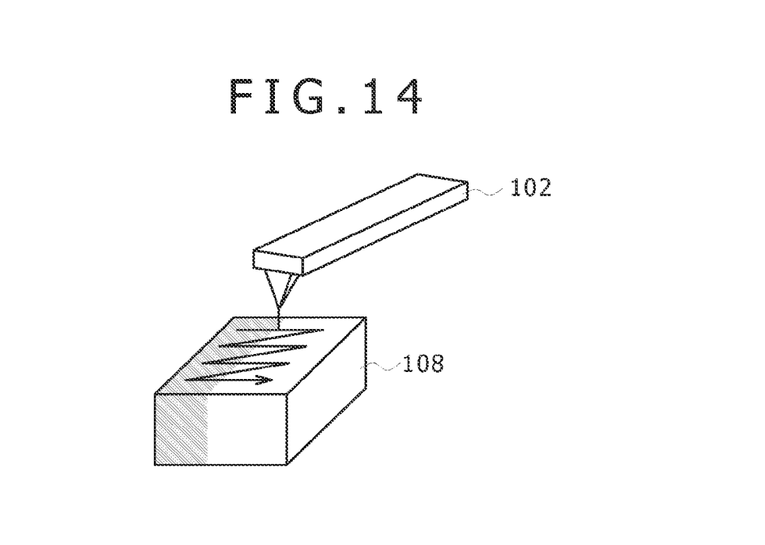
FIG. 14 is a schematic drawing showing the measurement of the surface of the sample by two-dimensional scanning by the cantilever.
Figure 15:
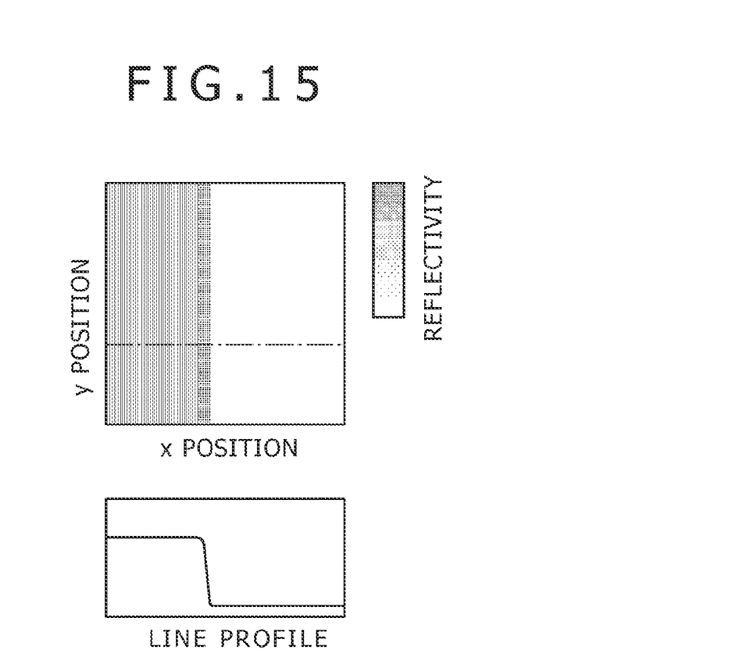
FIG. 15 shows an example of a result of the measurement.

The measurement method will be simply described below. A case that the cantilever 102 having the nanostructure 101 in which the near-field light 120 is excited at the end is two-dimensionally oscillated along the surface of the sample 108 for example as shown in FIG. 14 and the scattered light 122 of the near-field light 120 is measured is supposed. The distribution of reflectivity of the surface of the sample can be two-dimensionally visualized as shown in FIG. 15 for example by oscillating the cantilever 102 and mapping the intensity of the scattered light 122 at each point.

An example of the configuration of a concrete device shown in FIG. 1 will be described below. However, the details are omitted because each component has only to have the following function independent of the configuration. The controller 106 communicates with the PC 118, receives input from an operator, and can transmit a result of measurement to the PC 118. The controller 106 is configured by a part that acquires output from the sensor 105 and controls the scanner 107 for controlling the cantilever 102, a part that controls the sample stage 109, a part that controls the near-field light exciting laser 103, a part that receives a result of observation in the image sensor 111, a part that receives the information of the scattered light 122 detected by the photodetector 116 and a part that receives a result observed by the monitor 117. When modulation is applied to the sample 108, an oscillator and a circuit for it shall be provided.

A filter that extracts an arbitrary frequency component from a signal received from the photodetector 116 or a function that filters arbitrary plural frequency components and multiplexes results by a mixer and filters a generated beat shall be provided. Or a lock-in amplifier for acquiring a required signal shall be provided.

The embodiment described above merely shows one example of the embodiment of the present invention and a technical scope of the present invention should not be limitedly interpreted by these. That is, the present invention can be embodied in various modes without deviating from its technical idea or its primary characteristics.

What is claimed is:

1. A measurement method of a scanning probe microscope for observing a shape and an optical property of a sample by exciting near-field light, scanning relative positions of the near-field light and the sample and detecting scattered light of the near-field light by the sample, the method comprising:
    modulating the near-field light by modulating a laser light that excites the near field light and the sample;
    varying a relative distance between the near-field light and the sample; and
    selectively extracting an interference signal from the detected near field light generated by a frequency of modulation applied to the near-field light and a frequency for varying the relative distance between the near-field light and the sample.

2. The measurement method of the scanning probe microscope according to claim 1, wherein a plurality of frequencies are used to modulate the near-field light.

3. The measurement method of the scanning probe microscope according to claim 1, wherein, for a frequency of a selectively acquired signal, at least either of the sum of or difference between the frequency of the modulation applied to the near-field light and the frequency for varying the relative distance between the near-field light and the sample is selected.

4. The measurement method of the scanning probe microscope according to claim 1, wherein at least one of electric, optical, chemical, dynamic and thermal modulation is applied to the sample.

5. A scanning probe microscope, comprising:
    a near-field light exciting laser that excites near-field light;
    a cantilever that scans relative positions of the near-field light and a sample;
    a modulating device that modulates the near-field light by modulating a laser light that excites the near field light and the sample;
    a photodetector which is provided with a filter that selectively transmits a predetermined frequency and which detects scattered light of the near-field light by the sample; and
    a controller that causes the cantilever to oscillate, wherein the photodetector selectively extracts an interference signal from the detected near field light generated by a frequency of modulation applied to the near-field light and a frequency for varying the relative distance between the near-field light and the sample.

6. The scanning probe microscope according to claim 5, wherein the modulating device is a modulator that applies at least one of electric, optical, chemical, dynamic and thermal modulation to the sample.

7. The scanning probe microscope according to claim 5, wherein the modulating device is the near-field light exciting laser that radiates the modulated laser light and a modulator that applies at least one of electric, optical, chemical and dynamic modulation to the sample.

8. The scanning probe microscope according to claim 5, wherein a plurality of frequencies are modulated by the modulating device.

9. The scanning probe microscope according to claim 5, wherein the photodetector selects at least either of the sum of or difference between a frequency of modulation applied to the near-field light and a frequency for varying the relative distance between the near-field light and the sample as a frequency of a selectively acquired signal.

10. A measurement method of a scanning probe microscope for observing a shape and an optical property of a sample by exciting near-field light, scanning relative positions of the near-field light and the sample and detecting scattered light of the near-field light by the sample, the method comprising:

modulating the near-field light, such that an oscillation frequency of a cantilever and a modulation frequency of the near-field light are included in scattered light converged by a detecting lens;

varying a relative distance between the near-field light and the sample; and selectively extracting only frequency components corresponding to: i) a sum of the oscillation frequency of the cantilever and the modulation frequency of the near-field light, and ii) an absolute value of the modulation frequency of the near-field light minus the oscillation frequency of the cantilever, out of each frequency component included in the scattered light converged by the detecting lens.

11. The measurement method of the scanning probe microscope according to claim 10, wherein the near-field light is excited by laser light.

12. The measurement method of the scanning probe microscope according to claim 11, wherein a plurality of frequencies are used to modulate the near-field light.

13. The measurement method of the scanning probe microscope according to claim 12, wherein the near-field light is modulated by modulating the laser light.

14. The measurement method of the scanning probe microscope according to claim 13, wherein the near-field light is modulated by applying modulation to the sample.

15. The measurement method of the scanning probe microscope according to claim 14, wherein at least one of electric, optical, chemical, dynamic and thermal modulation is applied to the sample.

* * * * *